US009483117B2

(12) United States Patent
Karkkainen et al.

(10) Patent No.: US 9,483,117 B2
(45) Date of Patent: Nov. 1, 2016

(54) APPARATUS, METHOD AND COMPUTER PROGRAM FOR CONTROLLING A NEAR-EYE DISPLAY

(71) Applicant: Nokia Technologies Oy, Espoo (FI)

(72) Inventors: Leo Karkkainen, Helsinki (FI); Akos Vetek, Helsinki (FI); Jari Antero Kangas, Tampere (FI); Mikko Uusitalo, Helisnki (FI); Jukka Saarinen, Nokia (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 13/858,235

(22) Filed: Apr. 8, 2013

(65) Prior Publication Data

US 2014/0300532 A1    Oct. 9, 2014

(51) Int. Cl.
*G06F 3/01* (2006.01)
*G02B 27/01* (2006.01)
*A61B 5/11* (2006.01)
*A61B 5/00* (2006.01)

(52) U.S. Cl.
CPC ............ *G06F 3/015* (2013.01); *G02B 27/017* (2013.01); *G02B 27/0172* (2013.01); *G06F 3/012* (2013.01); *A61B 5/1122* (2013.01); *A61B 5/486* (2013.01); *A61B 5/6802* (2013.01); *A61B 5/6822* (2013.01); *G02B 2027/014* (2013.01); *G02B 2027/0187* (2013.01)

(58) Field of Classification Search
CPC .......... G06F 3/01; G06F 3/015; G06F 3/012; G02B 27/01; G02B 27/017; G02B 27/0172; G02B 2027/0187; G02B 2027/014; A61B 5/1122; A61B 5/6822; A61B 5/486; A61B 5/6802

USPC ......................................................... 345/156
See application file for complete search history.

(56) References Cited

U.S. PATENT DOCUMENTS

2009/0309808 A1* 12/2009 Swingler ............... G06F 3/1423
   345/1.3
2010/0151555 A1    6/2010 Julien et al.
(Continued)

FOREIGN PATENT DOCUMENTS

GB          2317086 A       3/1998

OTHER PUBLICATIONS

Barniv, Yair, et al.; "Using EMG to Anticipate Head Motion for Virtual-Environment Applications"; IEEE Transactions on Biomedical Engineering, vol. 52, No. 6, Jun. 2005, pp. 1078-1093; XP011132093.*

(Continued)

*Primary Examiner* — Andrew Sasinowski
(74) *Attorney, Agent, or Firm* — Alston & Bird LLP

(57) ABSTRACT

An apparatus, method and computer program where the apparatus comprises: at least one memory configured to store a computer program comprising computer program instructions; and at least one processor configured to execute the computer program instructions to cause the apparatus at least to perform: obtaining, from at least one detector, a detection of at least one bio-signal from at least one user where the user is using a user output device; determining from the at least one obtained bio-signal that movement of the user's head is about to occur; and in response to determining that movement of the user's head is about to occur, enabling the processor to control the output provided by the user output device to coordinate with the movement of the user's head.

20 Claims, 9 Drawing Sheets

(56) References Cited

U.S. PATENT DOCUMENTS

Figure 1:
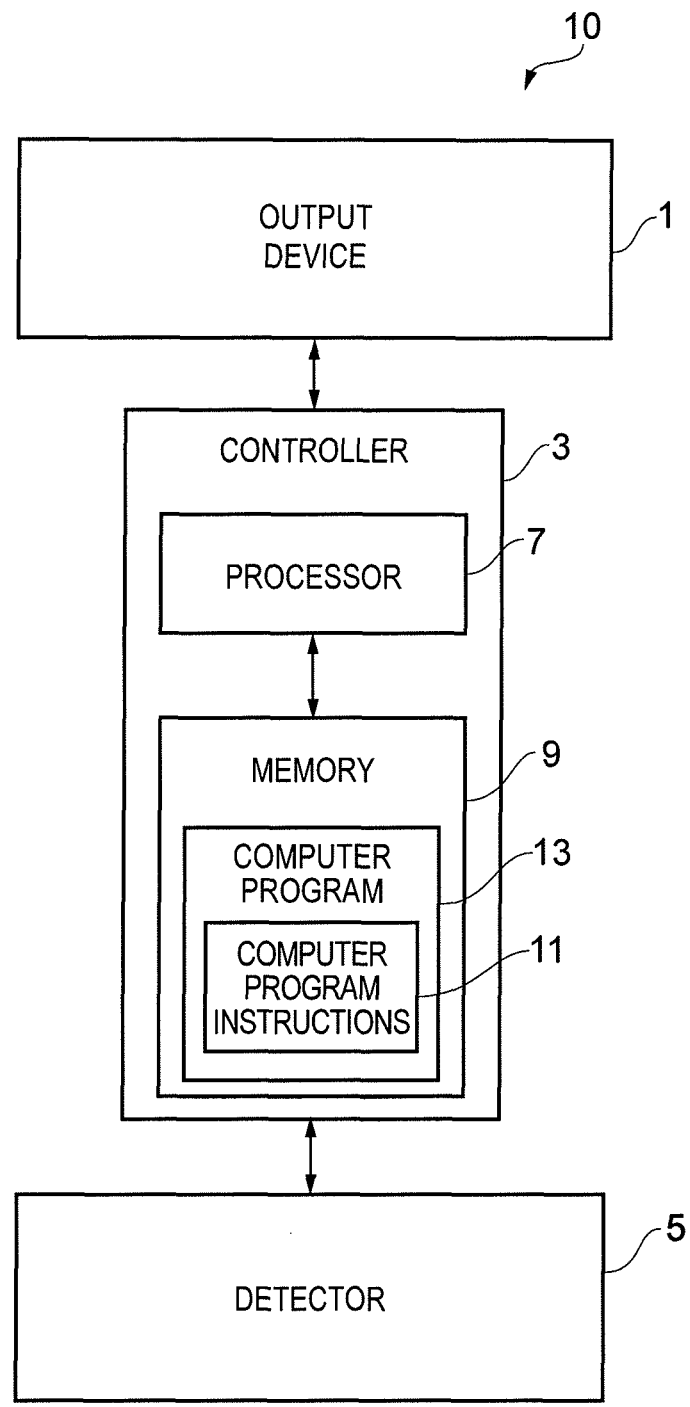

2012/0075183 A1* 3/2012 Liberty .................. 345/158
2012/0105473 A1 5/2012 Bar-Zeev et al.

OTHER PUBLICATIONS

Azuma, R. T., *Predictive Tracking for Augmented Reality*, Department of Computer Science, CB 3175, Sitterson Hall, UNC-Chapel Hill.
Di Fabio, R. P. et al., *Aging and the Mechanisms Underlying Head and Postural Control During Voluntary Motion*.
Foxling, E., *Chapter 7. Motion Tracking Requirements and Technologies*, InterSense Inc.
So, R. H., et al., *Target-directed Head Movements in a Head-coupled Virtual Environment: Predicting the Effects of Lags Using Fitt's Law*, Hong Kong University of Science and Technology.
Zangemeister, W. H., et al., *Simulation of Head Movement Trajectories: Model and Fit to Main Sequence*, Biol. Cybern. vol. 41 (1981) pp. 19-32.
Polak, Simon, et al.; "Head Motion Anticipation for Virtual-Environment Applications Using Kinematics and EMG Energy"; IEEE Transactions on Systems, Man, and Cybernetics—Part A: Systems and Humans, vol. 36, No. 3, May 2006; XP055122371.
Invitation to Pay Additional Fees and, Where Applicable, Protest Fee and Communication Relating to the Results of the Partial International Search Report from International Application No. PCT/IB2014/060423 mailed Jun. 18, 2014.
International Search Report and Written Opinion for Application No. PCT/IB2014/060423 dated Sep. 1, 2014.

* cited by examiner

APPARATUS, METHOD AND COMPUTER PROGRAM FOR CONTROLLING A NEAR-EYE DISPLAY

TECHNOLOGICAL FIELD

Embodiments of the present invention relate to an apparatus, method and computer program for controlling a user output device. In particular, they relate to an apparatus, method and computer program for controlling a user-output device when the user of the user output device is moving their head.

BACKGROUND

User-output devices such as displays or near-eye displays or three-dimensional audio systems may be used to provide outputs which are perceptible to a user. Near-eye displays are apparatus which enable an image to be provided proximate to the eye of the user. A user output device such as a near-eye display may be used in applications such as virtual reality or augmented reality applications. Apparatus such as near eye displays may be configured so as to enable overlaid viewing of virtual content and the real world.

It is useful to be able to control the images displayed on such displays or the outputs provided by such user output devices so that they are synchronised with movement of the user's head.

BRIEF SUMMARY

According to various, but not necessarily all, examples of the disclosure there may be provided an apparatus, comprising: at least one memory configured to store a computer program comprising computer program instructions; and at least one processor configured to execute the computer program instructions to cause the apparatus at least to perform: obtaining, from at least one detector, a detection of at least one bio-signal from at least one user where the user is using a user output device; determining from the at least one obtained bio-signal that movement of the user's head is about to occur; and in response to determining that movement of the user's head is about to occur, enabling the processor to control the output provided by the user output device to coordinate with the movement of the user's head.

In some examples the user output device may comprise a display.

In some examples the user output device may comprise a near-eye display.

In some examples the at least one bio-signal may comprise a bio-electrical signal.

In some examples the at least one bio-signal may be detected in a muscle of the user.

In some examples the at least one bio-signal may be detected in the user's neck muscles.

In some examples the at least one bio-signal may comprise a brain signal.

In some examples the at least one bio-signal may be detected using electromyography.

In some examples enabling the processor to control the output may comprise allocating processing capacity for coordinating the image displayed on a display with the movement of the user's head.

In some examples enabling the processor to control the output may comprise increasing a sampling rate of detectors configured to detect the movement of the user's head.

In some examples the at least one memory and processor may be configured to use the obtained bio-signal to predict a trajectory of movement of the user's head and the predicted trajectory is used to control the output provided. The shape and duration of an electrical pulse provided to a muscle may be used to predict the trajectory.

In some examples the at least one memory and processor may be configured to store information relating to obtained bio-signals and corresponding trajectories of head movement and use the stored information to predict trajectories of head movement in response to an obtained bio-signal.

According to various, but not necessarily all, examples of the disclosure there may be provided a method comprising: obtaining, from at least one detector, a detection of at least one bio-signal from at least one user where the user is using a user output device; determining from the at least one obtained bio-signal that movement of the user's head is about to occur; and in response to determining that movement of the user's head is about to occur, enabling the processor to control the output provided by the user output device to coordinate with the movement of the user's head.

In some examples the user output device may comprise a display.

In some examples the user output device may comprise a near-eye display.

In some examples the at least one bio-signal may comprise a bio-electrical signal.

In some examples the at least one bio-signal may be detected in a muscle of the user.

In some examples the at least one bio-signal may be detected in the user's neck muscles.

In some examples the at least one bio-signal may comprise a brain signal.

In some examples the at least one bio-signal may be detected using electromyography.

In some examples enabling the processor to control the output may comprise allocating processing capacity for coordinating the image displayed on a display with the movement of the user's head.

In some examples enabling the processor to control the output may comprise increasing a sampling rate of detectors configured to detect the movement of the user's head.

In some examples the method may also comprise using the obtained bio-signal to predict a trajectory of movement of the user's head and the predicted trajectory is used to control the output provided. The shape and duration of an electrical pulse provided to a muscle may be used to predict the trajectory.

In some examples the method may further comprise storing information relating to obtained bio-signals and corresponding trajectories of head movement and using the stored information to predict trajectories of head movement in response to an obtained bio-signal.

According to various, but not necessarily all, examples of the disclosure there may be provided a computer program comprising computer program instructions that, when executed by at least one processor, cause at least the following to be performed: obtaining, from at least one detector, a detection of at least one bio-signal from at least one user where the user is using a user output device; determining from the at least one obtained bio-signal that movement of the user's head is about to occur; and in response to determining that movement of the user's head is about to occur, enabling the processor to control the output provided by the user output device to coordinate with the movement of the user's head.

In some examples there may be provided a computer program comprising computer program instructions for causing a computer to perform the methods described above.

In some examples there may be provided a non-transitory computer readable medium comprising the computer program as described above.

In some examples there may be provided an electromagnetic carrier signal carrying the computer program as described above.

The apparatus may be for providing an output to a user. The apparatus may be for providing an image to a user in a virtual reality or augmented reality application.

BRIEF DESCRIPTION

Figure 2:
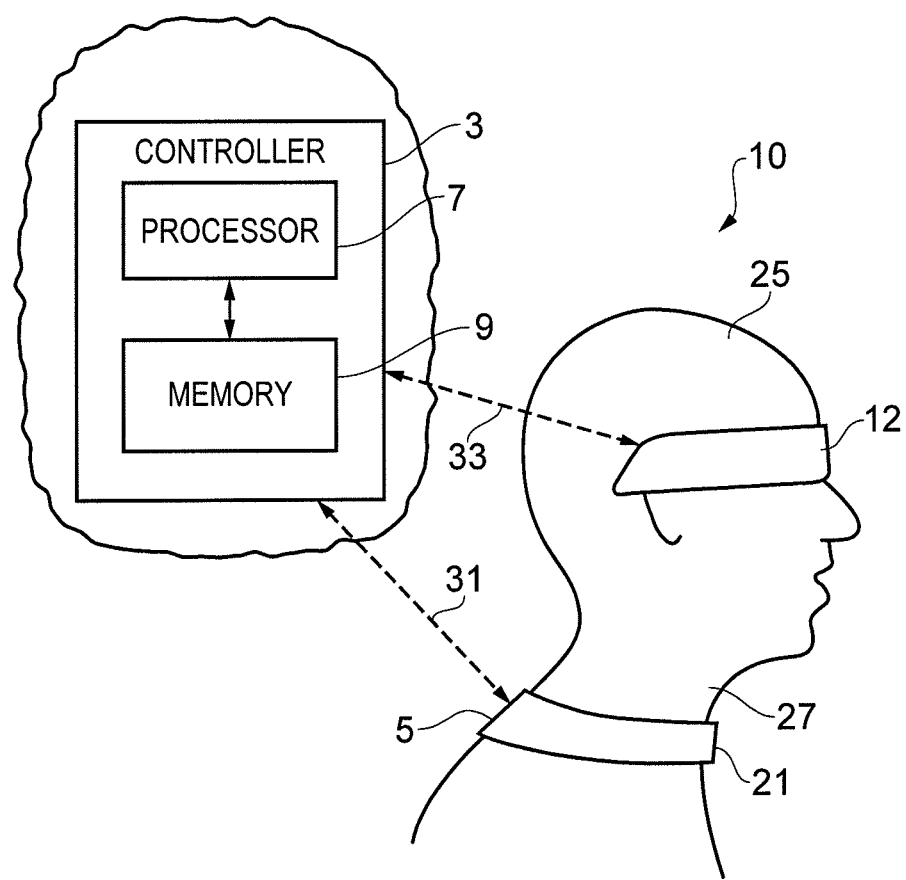
Figure 3:
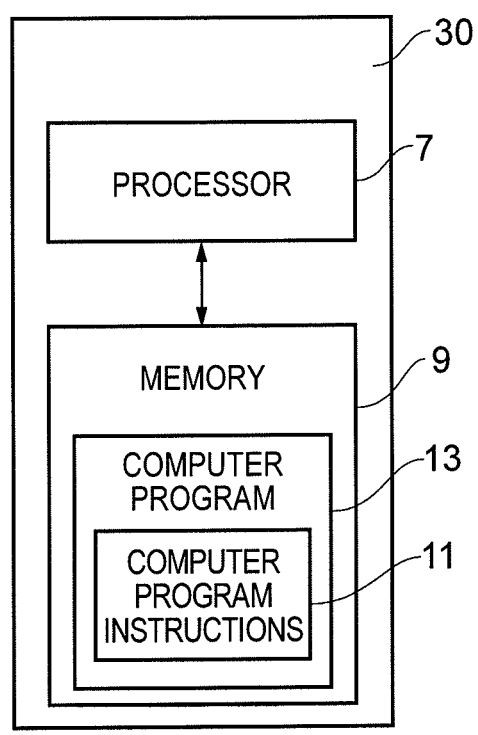
Figure 4:
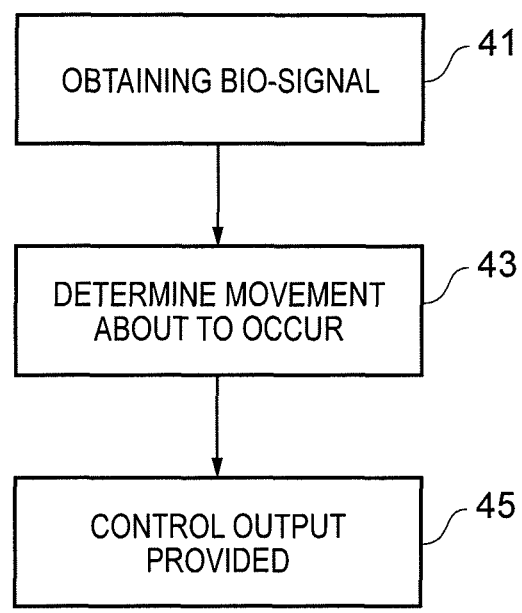
Figure 5:
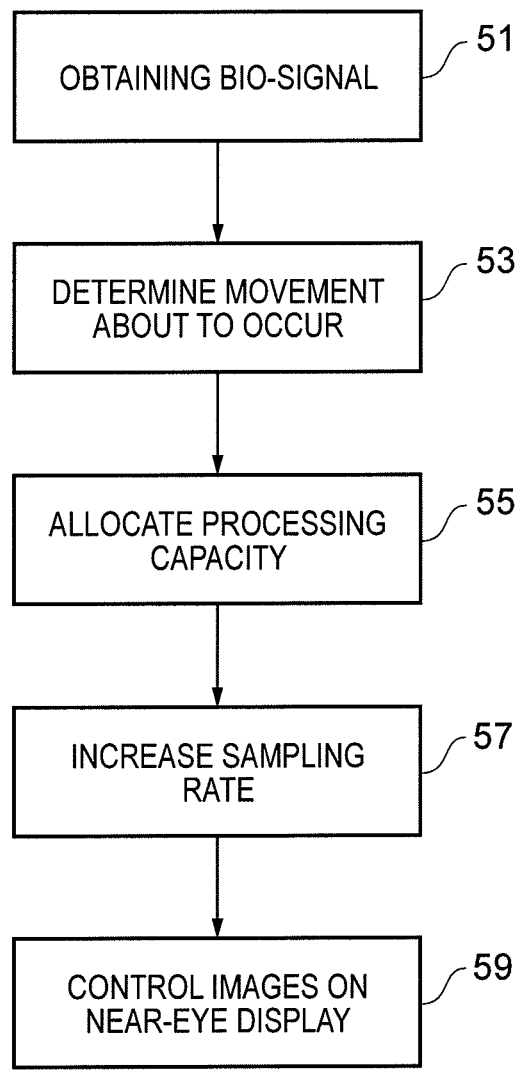
Figure 6:
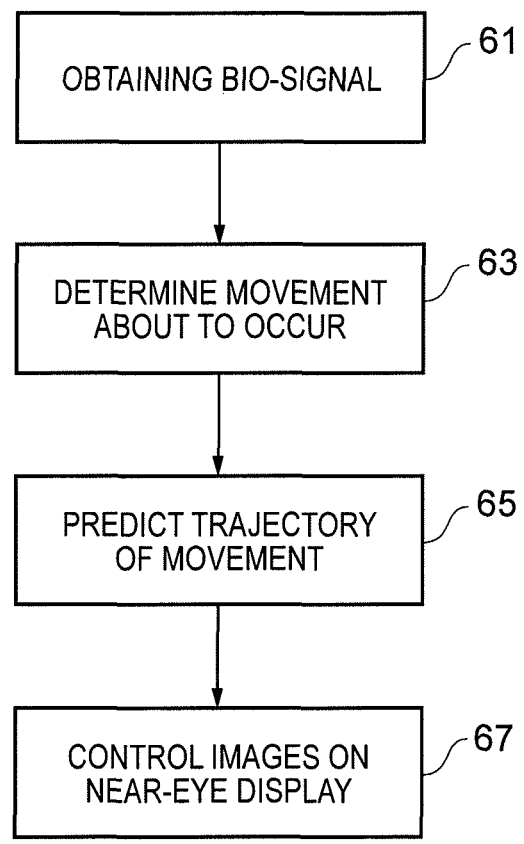
Figure 7A:
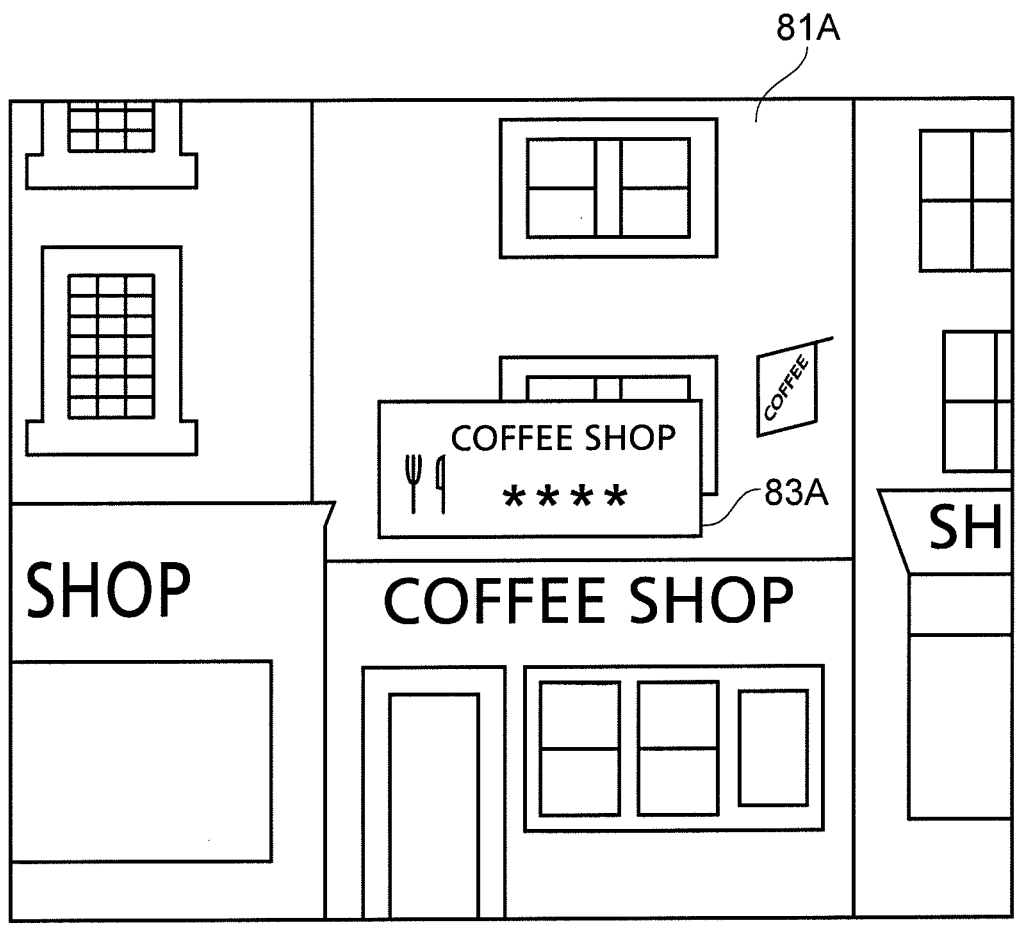
Figure 7B:
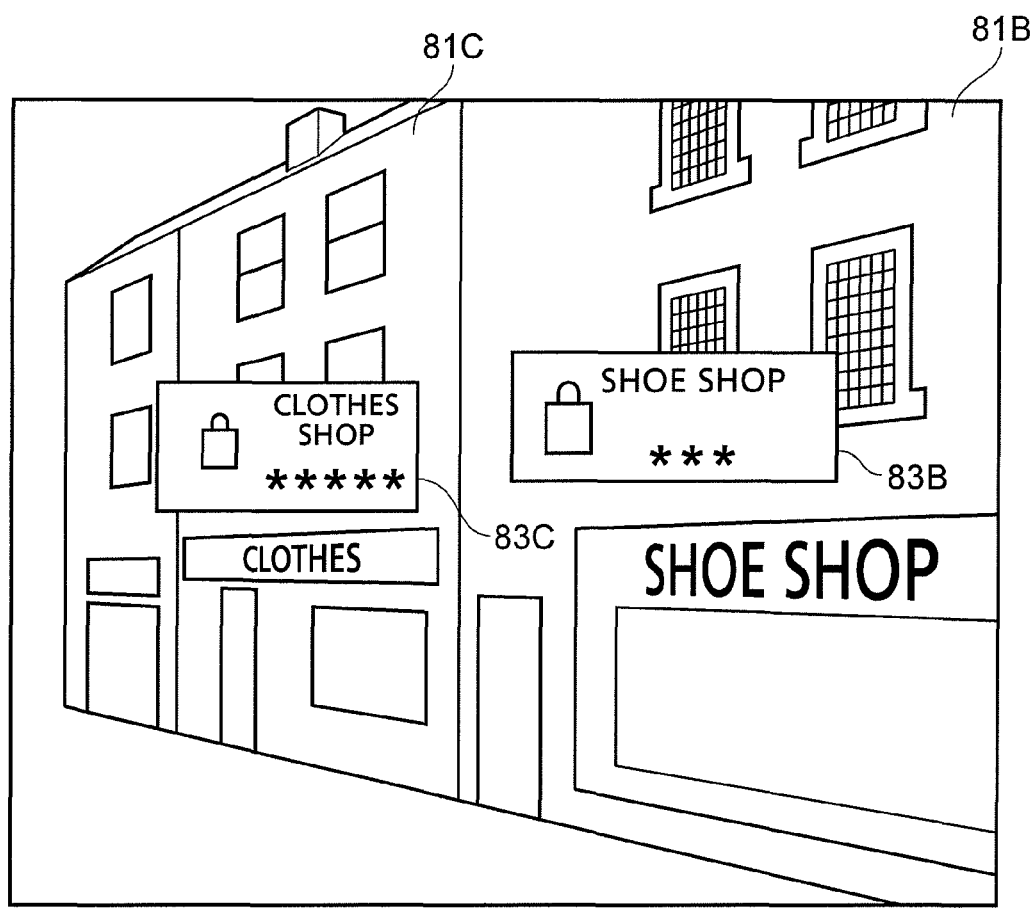
Figure 7C:
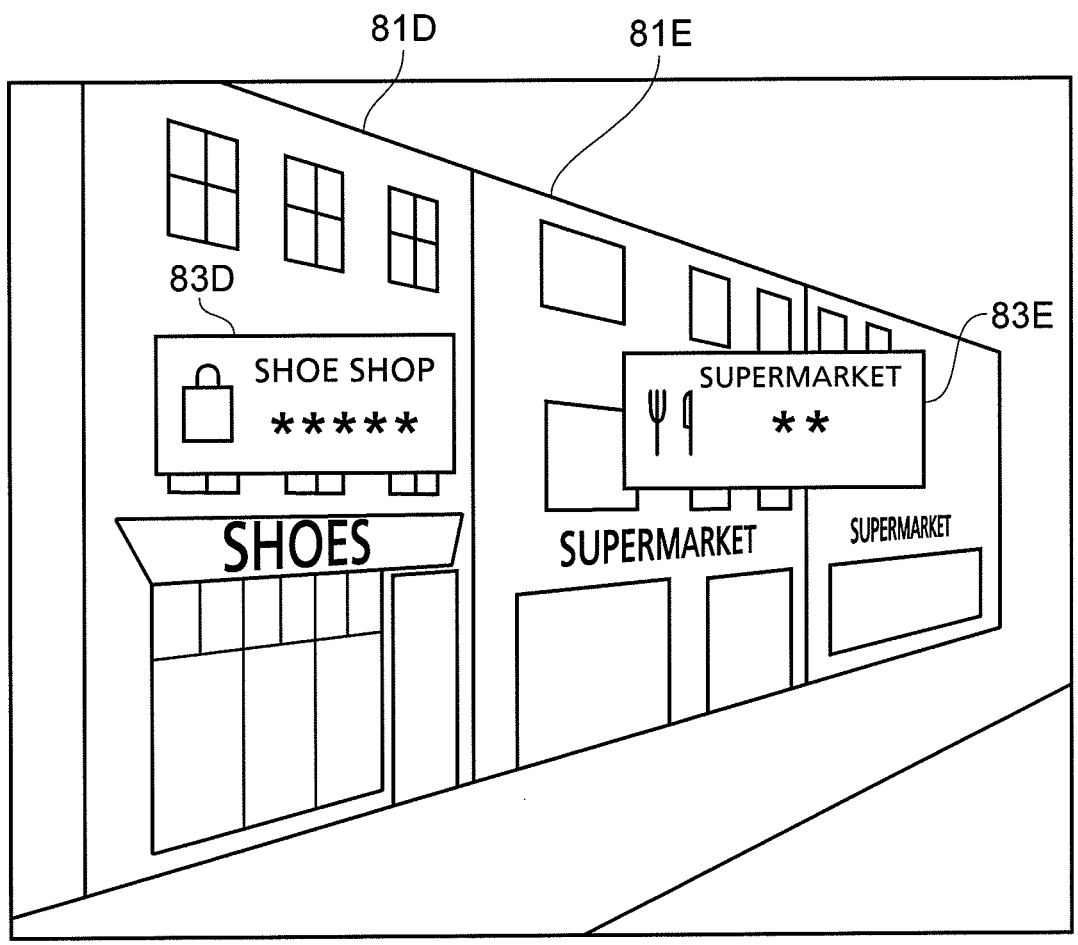

For a better understanding of various examples that are useful for understanding the detailed description, reference will now be made by way of example only to the accompanying drawings in which:

FIG. 1 illustrates a system;
FIG. 2 illustrates a system;
FIG. 3 illustrates an apparatus;
FIG. 4 illustrates a method;
FIG. 5 illustrates a method;
FIG. 6 illustrates a method; and
FIGS. 7A to 7C illustrate example images.

DETAILED DESCRIPTION

The Figures illustrate apparatus, methods and computer programs. The apparatus comprises: at least one memory 9 configured to store a computer program 13 comprising computer program instructions 11; and at least one processor 7 configured to execute the computer program instructions 11 to cause the apparatus at least to perform: obtaining, from at least one detector 5, a detection of at least one bio-signal from at least one user where the user is using a a user output device 1; determining from the at least one obtained bio-signal that movement of the user's head 25 is about to occur; and in response to determining that movement of the user's head 25 is about to occur, enabling the processor 7 to control the output provided by the user output device 1 to coordinate with the movement of the user's head 25.

FIG. 1 illustrates a system 10 according to examples of the disclosure. The system 10 comprises a user output device 1, a controller 3 and one or more detectors 5.

The user output device 1 may comprise a display 12. The display 12 may comprise means for displaying information. The display 12 may be configured to enable an image to be provided proximate to the eye of the user. The display 12 may comprise a near-eye display 12. The display 12 may be configured to provide a user with images which enable the user to use applications such as virtual reality and/or augmented reality applications.

In some examples the near-eye display 12 may be configured to be worn by the user. For example the near-eye display 12 may comprise a mounting portion which enables the near-eye display 12 to be mounted on the head or face of the user. When the near-eye display 12 is mounted on the head or face of the user, the user's head or face may support the weight or at least a portion of the weight of the near-eye display 12.

In other examples the user output device 1 may comprise means for providing an audio output. For example, the user output device 1 may comprise a loudspeaker or an earpiece. The user output device 1 may be worn by a user so that the loudspeaker may be positioned adjacent to the user's ears. In FIG. 1 only one user output device 1 is illustrated. It is to be appreciated that in other examples more than one user output device 1 may be provided.

The controller 3 may provide means for controlling the system 10. The controller 3 may be configured to obtain input signals from the one or more detectors 5. The controller 3 may be configured to control the images which are displayed on the display 12 or the audio outputs which are provided by a loudspeaker. In some examples the controller 3 may be configured to use the input signals provided by the one or more detectors 5 to control the images displayed on the display 12.

In the illustrated embodiment the controller 3 comprises at least one processor 7 and at least one memory 9. The processor 7 may be configured to read from and write to the at least one memory 9. The processor 7 may also comprise an output interface via which data and/or commands are output by the processor 7 and an input interface via which data and/or commands are input to the processor 7.

The controller 3 may be implemented using instructions that enable hardware functionality, for example, by using executable computer program instructions 11 in one or more general-purpose or special-purpose processors 7 that may be stored on a computer readable storage medium (e.g. disk, memory etc) to be executed by such processors 7.

The system 10 therefore comprises: at least one memory 9 configured to store a computer program 13 comprising computer program instructions 11; and at least one processor 7 configured to execute the computer program instructions 11 to cause an apparatus at least to perform obtaining, from at least one detector 5, a detection of at least one bio-signal from at least one user where the user is using a user output device 1; determining from the at least one obtained bio-signal that movement of the user's head is about to occur; and in response to determining that movement of the user's head is about to occur, enabling the processor 7 to control the output provided by the user output device 1 to coordinate with the movement of the user's head.

The at least one memory 9 may be configured to store a computer program 13 comprising computer program instructions 11 that control the operation of the system 10 when loaded into the at least one processor 7. The computer program instructions 11 provide the logic and routines that enable the system 10 to perform the example methods illustrated in FIGS. 4 to 6 and described below. The at least one processor 7 by reading the at least one memory 9 is able to load and execute the computer program 13.

The computer program instructions 11 may provide computer readable program means configured to control the system 10. The program instructions 11 may provide, when loaded into the controller 3; means for obtaining, from at least one detector 5, a detection of at least one bio-signal from at least one user where the user is using a user output device 1; means for determining from the at least one obtained bio-signal that movement of the user's head is about to occur; and means for, in response to determining that movement of the user's head is about to occur, enabling the processor 7 to control the output provided by the user output device 1 to coordinate with the movement of the user's head.

The computer program 13 may arrive at the controller 3 via any suitable delivery mechanism. The delivery mechanism may be, for example, a computer-readable storage medium, a computer program product, a memory device, a record medium such as a CD-ROM or DVD, or an article of manufacture that tangibly embodies the computer program 13. The delivery mechanism may be a signal configured to reliably transfer the computer program 13. The system 10 may propagate or transmit the computer program 13 as a computer data signal.

Although the memory 9 is illustrated as a single component it may be implemented as one or more separate components some or all of which may be integrated/removable and/or may provide permanent/semi-permanent/dynamic/cached storage.

Although the processor 7 is illustrated as a single component it may be implemented as one or more separate components some or all of which may be integrated/removable.

References to "computer-readable storage medium", "computer program product", "tangibly embodied computer program" etc. or a "controller", "computer", "processor" etc. should be understood to encompass not only computers having different architectures such as single/multi-processor architectures and sequential (e.g. Von Neumann)/parallel architectures but also specialized circuits such as field-programmable gate arrays (FPGA), application specific integration circuits (ASIC), signal processing devices and other devices. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" refers to all of the following:

(a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device."

The system 10 illustrated in FIG. 1 also comprises at least one detector 5. The detector 5 may comprise any means which is configured to detect one or more bio-signals and provide an indication of the detected bio-signal to the controller 3.

The bio-signals which are detected by the one or more detectors 5 may comprise any type of signal which originates from a user of the system 10. For example, the bio signal may originate from a user wearing a near-eye display 1. The bio-signals may, for example, comprise a bio-electrical signal, a bio-mechanical signal, an optical signal or any other suitable type of signal.

A bio-electrical signal may comprise an electrical current produced by one or more electrical potential differences across a part of the body of the user such as tissue, muscles, organ or cell system such as the nervous system. The detectors 5 may be configured to detect bio-electrical signals using electromyography (EMG), magnetoencephalography, electroencephalography (EEG) or any other suitable technique.

In some examples the system 10 may comprise one or more detectors 5 which may be configured to detect a bio-mechanical signal. A bio-mechanical signal may comprise the user of the apparatus 1 moving a part of their body. The detectors 5 may be configured to detect bio-mechanical signals using one or more accelerometers or mechanomyography or any other suitable technique.

In some examples the system 10 may comprise one or more detectors 5 which may be configured to detect an optical signal. An optical signal may comprise any signal which is visible. The detectors 5 may be configured to detect optical signals using a camera or any other means suitable for detecting optical signals.

In FIG. 1 only one detector 5 is illustrated. It is to be appreciated that in embodiments of the invention a plurality of detectors 5 may be provided. The plurality of detectors 5 may be configured to detect different types of bio-signals so that a range of different bio-signals may be obtained. For example, one or more detectors 5 could be configured to detect bio-electrical signals while one or more other detectors 5 could be configured to detect bio-mechanical signals.

In some examples the detectors 5 may be configured to be positioned close to a user to enable the bio-signals to be detected. For example the detectors 5 may comprise electrodes which may be positioned on the skin of the user or wearable electrodes or electrodes incorporated into fabrics or pieces of clothing.

In some examples the system 10 may be provided as a single apparatus. In such examples the display 12, controller 3 and one or more detectors 5 may be physically connected to each other. As an example the near-eye display 12 may comprise a head set which is configured to be worn by the user. The controller 3 may be provided within the headset and the one or more detectors 5 may extend out of the headset. It is to be appreciated that in other examples of the system 10 the user output device 1, controller 3 and one or more detectors 5 may be separated from each other. The separate components may be configured to communicate with the controller 3 via one or more communication links. An example of such a system is illustrated in FIG. 2.

FIG. 2 schematically illustrates a system 10 according to another example of the disclosure. The system 10 of FIG. 2 also comprises a display 12, a controller 3 and one or more detectors 5. The display 12, controller 3 and one or more detectors 5 may be as described above in relation to FIG. 1 and so the same reference numerals are used.

In the example of FIG. 2 the display comprises a near-eye display 12 which is mounted on the head 25 of the user. The near-eye display 12 may comprise a mounting portion 23 which may enable the near-eye display to be mounted on the head 25 of the user. In this particular example the near-eye display 12 is worn as a pair of glasses and the mounting portion 23 comprises arms which extend over the ears of the user. It is to be appreciated that in other examples other types of mounting portions 23 may be used.

In the example system of FIG. 2 one or more detectors 5 may be provided in a collar 21. The collar 21 may be worn around the neck 27 of the user. The detectors 5 in the collar 21 may be configured to detect bio-signals from the user's neck 27. For example, the detectors 5 may be configured to detect bio-electrical signals provided to the muscles in the user's neck. The bio-electrical signals which are provided to the muscles in the user's neck 27 may cause the movement of the user's head. The detectors 5 may be configured to detect bio-electrical signals provided to different muscles. Different muscles control different movements and so the muscle which the bio-electrical signal is provided to may provide an indication of the movement which is about to occur.

In some examples the collar 21 may comprise one or more detectors 5 which may be configured to detect actual movement of the user and/or the user's head 25. For example, the collar 21 may comprise detectors 5 which may be configured to determine the shape of the user's neck 27. The detectors 5 may be configured to detect a change in the shape of the user's neck which may result from the user moving their head 25.

It is to be appreciated that the system may comprise additional detectors 5 which are positioned outside of the collar 21.

The controller 3 may comprise a processor 7 and memory 9 as described above in relation FIG. 1. The memory 9 may be configured to store a computer program 13 comprising computer program instructions 11. The controller 3 may be part of a separate apparatus to the collar 21 and the near-eye display 12. In such examples the controller 3 may be configured to provide control signals to the near eye display 1 and the one or more detectors 5 via communication links 31, 33. The communication links 31, 33 may comprise wireless communication links. For example, in some systems 10 the controller 3 may be contained within a separate device such as the user's mobile phone. In other examples the controller 3 may be contained within the collar 21 or the mounting portion 23 of the near eye-display 12.

The controller 3 may be configured to obtain the detected bio-signals from the one or more detectors 5. The detectors 5 may be configured to transmit the detected bio-signals to the controller 3. The detectors 5 may be configured to transmit the detected bio-signals to the controller 3 via a communication link 31. The communication link 31 may comprise a wireless communication link.

The controller 3 may be configured to use the bio-signals obtained from the one or more detectors 5 to control the images displayed on the display 12. Examples of methods which may be implemented by the controller are described below in relation to FIGS. 4 to 6.

FIG. 3 illustrates an apparatus 30 according to another example of the disclosure. The apparatus 30 illustrated in FIG. 3 may be a chip or a chip-set. The apparatus 30 comprises at least one processor 7 and at least one memory 9 which may be configured as described above in relation to FIGS. 1 and 2.

FIGS. 3 to 6 schematically illustrate methods according to examples of the disclosure. The example methods may be implemented using systems 10 and apparatus 30 such as those described in FIGS. 1 to 3.

FIG. 4 illustrates a first example method which may be implemented using systems 10 and apparatus 30 such as those described in FIGS. 1 to 3.

The method comprises obtaining 41, from at least one detector 5 a detection of at least one bio-signal. The bio-signal may be obtained from the user of a user output device 1 such as a near-eye display 12. It is to be appreciated that other user output devices 1 may be provided in other examples. The method also comprises determining 43 that movement of the user's head 25 is about to occur. The bio-signal obtained at block 41 may be used to determine that the movement of the head 25 is about to occur.

The bio-signal which is obtained at block 41 may comprise any suitable signal.

In some examples the bio-signal may comprise a bio-electrical signal. The bio-electrical signal may be a signal such as a neural control signal which is provided from the brain of the user to the muscles of the user or a contraction of a muscle in a user's neck 27. If a bio-electrical signal is detected in the muscles of the user's neck 27 then this may provide an indication that a particular muscle is about to contract or relax which may cause movement of the user's head 25.

In some examples the bio-signal may comprise a muscle contraction. There may be detectable muscle contraction of a neck muscle 20 ms to 30 ms before the movement of the head. Therefore this may provide an indication that movement of the user's head 25 is about to occur.

In some examples the obtained bio-signal may comprise a brain signal. The brain signal may be detected using any suitable technique such as EEG. For example, the detectors 5 may be configured to detect activity in the areas of the brain used for coordinating movement such as the parietal cortex. The brain signals may be detectable before any bio-signals in the user's muscles. This may enable an even earlier indication that movement is about to occur.

Other bio-signals may also be detected. The other bio-signals may also provide an indication or suggestion that movement of the user's head 25 is about to occur. For example the detectors 5 may detect that a user has moved their arm or leg or other part of their body. In some examples the detectors 5 may detect that the user has moved their eyes. For example, the user may have started to look in a particular direction. This information could be used to predict that movement of the head is about to occur. In some examples it may be used to predict the trajectory of the head 25 movement. For example, if a user moves their hand and/or eyes towards the right it may be expected that they would also move their head 25 towards the right.

In response to determining that movement of the user's head 25 is about to occur the method comprises enabling 45 a processor 7 to control the output provided by a user output device 1. Controlling the output may comprise controlling the images displayed on the near-eye display 12. The processor 7 may control the images displayed on the near eye display 12 so that the images are coordinated with the movement of the head 25 of the user. This may enable virtual reality or augmented reality images to remain aligned with a user's head position.

The controller 3 may be configured to reduce any delay in detecting movement of the user's head 25 and controlling the images displayed on the display 12. For example, by using a detected bio-signal to determine that movement of the user's head 25 is about to occur the controller 3 can allocate capacity within the processor 7 for processing images before the movement begins. This can reduce the inherent processing delay. In some examples the detected bio-signals may be used to predict the actual trajectory of the movement of the head 25 and this predicted trajectory may be used by the processor 7 to control the images displayed on the display 12.

FIG. 5 illustrates another method which may be implemented by the systems 10 and apparatus 30 of FIGS. 1 to 3.

The method of FIG. 5 also comprises obtaining 51, from at least one detector 5 a detection of at least one bio-signal where the bio-signal may be obtained from the user of a display such as a near eye-display 1. The method of FIG. 5 may also comprise determining 53 that movement of the user's head is about to occur. The bio-signal obtained at block 51 may be used to determine that the movement of the head 25 is about to occur.

As described above with respect to FIG. 4 the detected bio-signal may comprise any suitable signal such as a bio-electrical signal or a bio-mechanical signals or any other type of bio-signal.

In response to determining that movement of the user's head is about to occur, the example method of FIG. 5 comprises allocating 55 processing capacity so as to enable the images displayed on a display 12 to be coordinate with the movement of the user's head 25. This may reduce any delay between actual movement of the user's head 25 and the control of the images displayed on the display 12.

In response to determining that movement of the user's head 25 is about to occur the example method of FIG. 5 may also comprise increasing 57 a sampling rate of one or more detectors 5. For example the system 10 may comprise detectors 5 which may be configured to detect the movement of the users head. For example the system 10 may comprises one or more motion detectors 5. The motion detectors 5 may be configured to detect movement of the user's head 25. If it is determined that movement of the user's head 25 is about to occur then the sampling rate of the motion detectors 5 may be increased so as to reduce any delay in movement of the users head 25 and the images displayed on the display 12.

At block 59 the processor 7 controls the images displayed on the near eye display 12 so that the images are coordinated with the movement of the head 25 of the user.

In some examples, signals obtained from other detectors 5 may be used to predict probable head 25 positions. For example the movement or positions of other parts of the user's body such as their arms or legs may provide an indication of probable head 25 movements.

FIG. 6 illustrates another method which may also be implemented using systems 10 and apparatus 30 such as those illustrated in FIGS. 1 to 3.

The method of FIG. 6 comprises obtaining 61, from at least one detector 5 a detection of at least one bio-signal and determining 63 that movement of the user's head is about to occur. The bio-signal obtained at block 61 may be used to determine that the movement of the head 25 is about to occur.

The detected bio-signal may comprise any suitable signal. The detected bio-signal may be used, at block 65, to predict the trajectory of the movement of the user's head 25. For example, the detectors 5 may be configured to detect a control signal provided to a neck muscle or contraction of a neck muscle. By determining which neck muscle is about to move the trajectory of the head 25 movement may be predicted. For example the sternocleidomastoid muscles and scalene muscles control lateral head movements. If a bio-signal is detected from the sternocleidomastoid muscles and/or scalene muscles this may provide an indication that lateral movement of the head 25 is about to occur. Similarly the deep splenius muscles and the superficial trapezius muscles control head extension. If a bio-signal is detected from the deep splenius muscles and/or the superficial trapezius muscles this may provide an indication that extension of the head 25 is about to occur.

In some examples the bio-signals may comprise control signals which are provided to the muscles. The control signals may be detect using any suitable technique such as EMG. The intensity and duration of pulses within the control signals may provide an indication of the trajectory of the head movement. For example it may provide an indication of the speed of the magnitude of the movement. For example, it may provide an indication of the amount that the user is about to rotate their head or the speed or accelerations of the movement.

At block 67 the predicted trajectory may be used by the processor 7 to control the images displayed on the display according to the predicted trajectory.

In some examples the system 10 may implement adaptive algorithms which may be used to improve the alignment of the images displayed on the display 12 when the user moves their head. For example a camera or other detector 5 may be used to determine if there is any lag between the images displayed on the display 12 and the position of the user's head 25. The controller 4 may then use this information to adapt the response to detected bio-signals to reduce any detected lag. This may improve the accuracy of the system 10.

The use of the adaptive algorithms may comprise storing information relating to obtained bio-signals and a corresponding measured trajectory. The information may be stored in the one or more memories 9 of the controller 3. The stored information may be used to predict trajectories of head 25 movement by making comparisons to previously detected bio-signals.

The adaptive algorithms may be used to calibrate the systems 10 prior to use and/or during use. For example the detectors 5 might not always be positioned in exactly the same position and so there may be differences in the detected bio-signals every time the user the uses the system 10. The adaptive algorithms may be configured to correct for such instances.

The adaptive algorithms used may comprise any suitable algorithms such as kalman filters.

The systems 10, apparatus 30 and methods described above reduce any lag between an output provided by a user output device 1 and the position of a user's head 25. In some examples the system 10 may reduce any lag between the images displayed on a display such as a near-eye display 12 and the head 25 position of the user. This may be particularly advantageous for augmented reality and virtual reality applications.

The system 10 and apparatus 30 may be able to reduce the lag in the images displayed on the display so that the images displayed on the display 1 can change simultaneously with the head movement. This may allow for a flow of images as the user moves their head 25. This may make the augmented reality and/or virtual reality applications more realistic.

FIGS. 7A to 7C illustrate example images which may be displayed on a display such as a near eye display 12 in a system 10 implementing methods as described above.

In the examples of FIGS. 7A to 7C the images may be augmented reality images. The example images may comprise real world images of the user's real location which are then augmented with additional information or images overlaying the real world image. In the particular example of FIGS. 7A to 7C the real world images comprise a plurality of buildings in a street. These images of the buildings are augmented with additional information relating to the shops or businesses located within the buildings. The augmented reality application may be for example, Nokia city lens or any other suitable application.

In FIG. 7A the user has their head 25 positioned so that they are looking straight forward. The controller 3 controls the near-eye display 12 to display an image of a coffee shop 81A which is located straight ahead of the user. The image of the coffee shop 81 is augmented with an icon 83A. The controller 3 controls the images displayed on the near-eye display 12 so that the icon 83A associated with the coffee shop 81 is displayed overlaying the coffee shop.

In the example of FIG. 7A the icon 83A may comprise information relating to the coffee shop. In this particular example the icon 83A contains a rating of the coffee shop 81A. The rating maybe rating given by a user of the system 10 or by other user's of the coffee shop.

The user may then move their head 25 so that they are no longer looking straight forward. In FIG. 7B the user has rotated their head 25 towards their left hand side. As described above the detector 5 may detect bio-signals which indicate that the user is about to move their head 25. The controller 3 may determine that the user is about to rotate their head 25 to the left. The controller 3 then controls the near-eye display 12 so that the images displayed on the near-eye display 12 are coordinated with the user's head 25 movement. The controller 3 may control the near-eye display 12 so that the images displayed on the display are changed simultaneously with the movement of the user's head 25.

In FIG. 7B the user has moved their head to the left so that they are now looking towards different buildings 81B and 81C. The image of the coffee shop 81A has been removed from the near-eye display 12 and an image of a clothes shop 81C and a shoe shop 81B is now displayed on the near-eye display 12. Icons 83B and 83C providing further information relating to the clothes shop 81C and shoe shop 81B are providing overlaying the images of the clothes shop 81C and shoe shop 81B respectively.

In the example of FIG. 7C the user has rotate their head 25 towards their right hand side. As described above the detector 5 may detect bio-signals which indicate that the user is about to move their head 25 and the controller 3 may determine that the user is about to rotate their head 25 to the right. The controller 3 controls the near-eye display 12 so that the images displayed on the near-eye display 12 are coordinated with the rotation of the user's head 25. The controller 3 may control the near-eye display 12 so that the images displayed on the display are changed simultaneously with the movement of the user's head.

In FIG. 7C the user has moved their head to the right so that they are now looking towards the buildings on the right hand side of the coffee shop 81A. The image of the coffee shop 81A has been removed from the near-eye display 12 and an image of another shoe shop 81D and a supermarket 81E is now displayed on the near-eye display 12. Icons 83D, 83E providing further information relating to the another shoe shop 81D and supermarket 81E are provided overlaying the images of the shoe shop 81D and supermarket 81E respectively.

In the above described example of FIGS. 7A to 7C the system is used to provide additional information about local businesses. It is to be appreciated that other augmented reality applications may be used to provide other information to the user. For example, in some applications a translation of the signs on the streets or businesses may be provided overlaying the real world images. In other examples information which may be useful for maintenance workers may be provided overlaying the real world images.

It is to be appreciated that examples of the disclosure may be used in a range of implementations. In some implementations the system may provide a virtual reality applications to a use. The virtual reality applications may be for example a driving or flight simulator which may be used for learning or training or playing games. Examples of the disclosure may provide a more realistic user experience because it would minimise the lag between the movement of the user's head 25 and the output provided by the output devices 1.

The blocks illustrated in the FIGS. 3 to 6 may represent steps in a method and/or sections of code in the computer program 13. The illustration of a particular order to the blocks does not necessarily imply that there is a required or preferred order for the blocks and the order and arrangement of the block may be varied. Furthermore, it may be possible for some blocks to be omitted. For example, in the method of FIG. 5 in some systems the block of increasing the sampling rate of detectors may be omitted or replaced with another block such as predicting a possible head 25 position.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In the detailed description, reference has been made to various examples. The description of features or functions in relation to an example indicates that those features or functions are present in that example. The use of the term "example" or "for example" or "may'" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class.

Although embodiments of the present invention have been described in the preceding paragraphs with reference to various examples, it should be appreciated that modifications to the examples given can be made without departing from the scope of the invention as claimed. For example in some examples the user output device 1 may comprise an earpiece and the audible output provided by the earpiece may be controlled to be co-ordinated with the user's head 25 position.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus, comprising:
  at least one non-transitory memory configured to store a computer program comprising computer program instructions; and
  at least one processor configured to execute the computer program instructions to cause the apparatus at least to perform:

obtaining, from at least one detector, a detection of at least one bio-signal from at least one user where the user is using a user output device;

determining from the at least one obtained bio-signal that movement of the user's head is about to occur; and in response to determining that movement of the user's head is about to occur, enabling the processor to control the output provided by the user output device to coordinate with the movement of the user's head, wherein enabling the processor to control the output comprises, in response to determining that movement of the user's head is about to occur, allocating processing capacity for later processing, wherein the later processing comprises processing images for coordinating the image displayed on a display with the movement of the user's head.

2. An apparatus as claimed in claim 1 wherein the user output device comprises at least one of a display, or a near-eye display.

3. An apparatus as claimed in claim 1 wherein the at least one bio-signal comprises a bio-electrical signal.

4. An apparatus as claimed in claim 1 wherein the at least one bio-signal is detected in at least one of a muscle of the user, or the user's neck muscles.

5. An apparatus as claimed in claim 1 wherein the at least one bio-signal comprises a brain signal.

6. An apparatus as claimed in claim 1 wherein the at least one bio-signal is detected using electromyography.

7. An apparatus as claimed in claim 1 wherein enabling the processor to control the output comprises increasing a sampling rate of detectors configured to detect the movement of the user's head.

8. An apparatus as claimed in claim 7 wherein the shape and duration of an electrical pulse provided to a muscle is used to predict the trajectory.

9. An apparatus as claimed in claim 1 wherein the at least one non-transitory memory and processor are configured to use the obtained bio-signal to predict a trajectory of movement of the user's head and the predicted trajectory is used to control the output provided.

10. An apparatus as claimed in claim 1 wherein the at least one non-transitory memory and processor are configured to store information relating to obtained bio-signals and corresponding trajectories of head movement and use the stored information to predict trajectories of head movement in response to an obtained bio-signal.

11. An apparatus as claimed in claim 1 wherein the processing capacity allocated in response to determining that movement of the user's head is about to occur is temporarily allocated.

12. A method comprising:

obtaining, from at least one detector, a detection of at least one bio-signal from at least one user where the user is using a user output device;

determining from the at least one obtained bio-signal that movement of the user's head is about to occur; and in response to determining that movement of the user's head is about to occur, enabling the processor to control the output provided by the user output device to coordinate with the movement of the user's head, wherein enabling the processor to control the output comprises, in response to determining that movement of the user's head is about to occur, allocating processing capacity for later processing, wherein the later processing comprises processing images for coordinating the image displayed on a display with the movement of the user's head.

13. A method as claimed in claim 12 wherein the at least one bio-signal comprises a bio-electrical signal.

14. A method as claimed in claim 12 wherein the at least one bio-signal is detected in at least one of a muscle of the user, or the user's neck muscles.

15. A method as claimed in claim 12 wherein the at least one bio-signal comprises a brain signal.

16. A method as claimed in claim 12 wherein the at least one bio-signal is detected using electromyography.

17. A method as claimed in claim 12 wherein enabling the processor to control the output comprises increasing a sampling rate of detectors configured to detect the movement of the user's head.

18. A method as claimed in claim 12 further comprising using the obtained bio-signal to predict a trajectory of movement of the user's head and the predicted trajectory is used to control the output provided and the shape and duration of an electrical pulse provided to a muscle is used to predict the trajectory.

19. A method as claimed in claim 12 further comprising storing information relating to obtained bio-signals and corresponding trajectories of head movement and using the stored information to predict trajectories of head movement in response to an obtained bio-signal.

20. A non-transitory computer readable medium comprising a computer program comprising computer program instructions that, when executed by at least one processor, cause at least the following to be performed:

obtaining, from at least one detector, a detection of at least one bio-signal from at least one user where the user is using a user output device;

determining from the at least one obtained bio-signal that movement of the user's head is about to occur; and in response to determining that movement of the user's head is about to occur, enabling the processor to control the output provided by the user output device to coordinate with the movement of the user's head, wherein enabling the processor to control the output comprises, in response to determining that movement of the user's head is about to occur, allocating processing capacity for later processing, wherein the later processing comprises processing images for coordinating the image displayed on a display with the movement of the user's head.

* * * * *